(12) United States Patent
Swift

(10) Patent No.: US 10,722,621 B2
(45) Date of Patent: Jul. 28, 2020

(54) ILLUMINATED SUCTION DEVICE

(71) Applicant: OBP Medical Corporation, Lawrence, MA (US)

(72) Inventor: Jeffrey Ralph Swift, Lawrence, MA (US)

(73) Assignee: OBP MEDICAL CORPORATION, Lawrence, MA (US)

( * ) Notice: Subject to any disclaimer, the term of this patent is extended or adjusted under 35 U.S.C. 154(b) by 95 days.

(21) Appl. No.: 15/646,372

(22) Filed: Jul. 11, 2017

(65) Prior Publication Data

US 2018/0008754 A1    Jan. 11, 2018

Related U.S. Application Data

(60) Provisional application No. 62/360,810, filed on Jul. 11, 2016, provisional application No. 62/441,645, filed on Jan. 3, 2017.

(51) Int. Cl.
*A61M 1/00* (2006.01)
*F21V 33/00* (2006.01)
(Continued)

(52) U.S. Cl.
CPC ............ *A61M 1/008* (2013.01); *A61B 90/30* (2016.02); *A61M 1/0039* (2013.01); *F21V 23/04* (2013.01); *F21V 33/0068* (2013.01); *A61B 2018/0091* (2013.01); *A61B 2090/309* (2016.02); *A61B 2505/05* (2013.01); *A61M 2205/3317* (2013.01); *A61M 2205/587* (2013.01);
(Continued)

(58) Field of Classification Search
CPC ....... A61B 90/30; A61B 18/18; A61B 90/306; A61B 17/3476; A61B 2018/00589; A61B 2018/00607; A61B 1/0669; A61B 2217/005

See application file for complete search history.

(56) References Cited

U.S. PATENT DOCUMENTS

| 559,122 A | 4/1896 | Daily |
| 659,182 A | 10/1900 | Pilling |

(Continued)

FOREIGN PATENT DOCUMENTS

| CN | 2239235 Y | 11/1996 |
| CN | 2265156 Y | 10/1997 |

(Continued)

OTHER PUBLICATIONS

The above foreign patent document 1 was cited in the Jul. 16, 2018 Chinese Office Action, which is enclosed without an English Translation, that issued in Chinese Patent Application No. 201510543086.7.

(Continued)

*Primary Examiner* — David W Bates
(74) *Attorney, Agent, or Firm* — Cowan, Liebowitz & Latman, P.C.; Anastasia Zhadina

(57) ABSTRACT

An exemplary embodiment comprises an illuminated suction device having a distal end with a suction tip; a proximal end with a connector for a suction tube; and an illumination assembly comprising at least one light source, at least one battery and an activation device for energizing the light source, the illumination assembly being permanently attached to the suction device.

17 Claims, 10 Drawing Sheets

(51) Int. Cl.
*F21V 23/04* (2006.01)
*A61B 90/30* (2016.01)
*F21W 131/20* (2006.01)
*A61B 18/00* (2006.01)
*F21Y 115/10* (2016.01)

(52) U.S. Cl.
CPC . *A61M 2205/8206* (2013.01); *F21W 2131/20* (2013.01); *F21Y 2115/10* (2016.08)

(56) References Cited

U.S. PATENT DOCUMENTS

| | | |
|---|---|---|
| 2,235,979 A | 3/1941 | Brown |
| 2,247,458 A | 6/1941 | Shepard |
| 2,482,971 A | 9/1949 | Golson |
| 2,592,190 A | 4/1952 | Rubens et al. |
| 3,324,850 A | 6/1967 | Gunning et al. |
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |
| 3,638,644 A | 2/1972 | Reick |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitman |
| 3,815,585 A | 6/1974 | Fiore |
| 3,826,248 A | 7/1974 | Gobels |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A | 7/1982 | Petrassevich |
| 4,343,300 A * | 8/1982 | Hattori ............... A61B 1/00059 396/17 |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie et al. |
| 5,499,964 A | 3/1996 | Beck et al. |
| 5,512,038 A | 4/1996 | O'Neal et al. |
| 5,553,627 A | 9/1996 | Newkirk |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Shuchman et al. |
| 5,888,195 A | 3/1999 | Schneider |
| 5,899,854 A | 5/1999 | Slishman |
| 5,902,315 A | 5/1999 | Dubois |
| 5,916,150 A | 6/1999 | Sillman |
| 6,001,077 A | 12/1999 | Ellman et al. |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,193,653 B1 | 2/2001 | Evans et al. |
| 6,217,512 B1 | 4/2001 | Salo et al. |
| 6,231,505 B1 | 5/2001 | Martin |
| 6,231,506 B1 | 5/2001 | Hu et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,413,208 B1 | 7/2002 | Schollhorn et al. |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,089 B1 * | 5/2003 | Covington ............. A61B 1/267 600/199 |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |
| 7,276,025 B2 | 10/2007 | Roberts et al. |
| 7,306,559 B2 | 12/2007 | Williams |
| 7,631,981 B2 | 12/2009 | Miller et al. |
| 7,736,304 B2 | 6/2010 | Pecherer |
| 7,758,203 B2 | 7/2010 | McMahon et al. |
| 7,878,973 B2 | 2/2011 | Yee et al. |
| 7,909,759 B2 | 3/2011 | Pecherer |
| 7,967,809 B2 | 6/2011 | Jay-Robinson |
| 8,012,089 B2 | 9/2011 | Bayat |

(56) References Cited

U.S. PATENT DOCUMENTS

| | | |
|---|---|---|
| 8,047,987 B2 | 11/2011 | Grey et al. |
| 8,052,702 B2 | 11/2011 | Hess et al. |
| 8,088,066 B2 | 1/2012 | Grey et al. |
| 8,096,945 B2 | 1/2012 | Buchok et al. |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,292,805 B2 | 10/2012 | Vayser et al. |
| 8,317,693 B2 | 11/2012 | Grey et al. |
| 8,348,838 B1 * | 1/2013 | Khurgin .............. A61M 1/008 600/212 |
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |
| 8,555,892 B2 | 10/2013 | Traub |
| 8,596,847 B2 | 12/2013 | Vayser et al. |
| 8,628,879 B2 | 1/2014 | Pecherer et al. |
| 8,795,162 B2 | 8/2014 | Vayser et al. |
| 8,821,385 B2 | 9/2014 | Naito |
| 8,870,761 B2 | 10/2014 | Vayser et al. |
| D719,652 S | 12/2014 | Swift |
| 8,979,745 B2 | 3/2015 | Swift |
| 9,044,161 B2 | 6/2015 | Vayser et al. |
| 9,050,048 B2 | 6/2015 | Nadershahi et al. |
| 9,072,452 B2 | 7/2015 | Vayser et al. |
| D745,669 S | 12/2015 | Swift |
| 9,241,617 B2 | 1/2016 | Grey et al. |
| D752,217 S | 3/2016 | Swift |
| 9,271,709 B2 | 3/2016 | Grey et al. |
| 9,271,710 B2 | 3/2016 | Grey et al. |
| 9,282,878 B2 | 3/2016 | Grey et al. |
| D753,295 S | 4/2016 | Vivenzio et al. |
| 9,307,897 B2 | 4/2016 | Swift |
| 9,308,054 B2 | 4/2016 | Vayser et al. |
| 9,332,898 B2 | 5/2016 | McMahon et al. |
| 9,468,366 B2 | 10/2016 | Grey et al. |
| 9,510,737 B2 | 12/2016 | Vayser et al. |
| 9,532,706 B2 | 1/2017 | McMahon et al. |
| 9,629,529 B1 | 4/2017 | Indovina et al. |
| 9,636,182 B2 | 5/2017 | Vayser et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,833,308 B2 | 12/2017 | Dye |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ahn |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 2001/0029044 A1 | 10/2001 | Gombrich et al. |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0115909 A1 | 8/2002 | Bolser |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0095781 A1 | 5/2003 | Williams |
| 2003/0139673 A1 | 7/2003 | Vivenzio et al. |
| 2003/0158502 A1 | 8/2003 | Baxter-Jones et al. |
| 2003/0176772 A1 | 9/2003 | Yang |
| 2003/0187331 A1 | 10/2003 | Faludi et al. |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2005/0065496 A1 | 3/2005 | Simon et al. |
| 2005/0085699 A1 | 4/2005 | Weiss |
| 2005/0085723 A1 | 4/2005 | Huebner |
| 2005/0125015 A1 | 6/2005 | McNally-Heintzelman et al. |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0155276 A1 | 7/2006 | Walulik et al. |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0066872 A1 | 3/2007 | Morrison et al. |
| 2007/0100212 A1 | 5/2007 | Pimenta et al. |
| 2007/0174947 A1 * | 8/2007 | Schneider ............ A61B 42/10 2/161.1 |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2007/0287888 A1 | 12/2007 | Lovell et al. |
| 2008/0002426 A1 | 1/2008 | Vayser et al. |
| 2008/0113312 A1 | 5/2008 | Ortega |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 * | 11/2008 | Kurth ............... F21L 4/027 362/191 |
| 2009/0018400 A1 | 1/2009 | Raymond et al. |
| 2009/0069634 A1 | 3/2009 | Larkin |
| 2009/0097236 A1 | 4/2009 | Miller et al. |

(56) References Cited

U.S. PATENT DOCUMENTS

| | | |
|---|---|---|
| 2009/0112068 A1 | 4/2009 | Grey et al. |
| 2009/0275603 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0191062 A1 | 7/2010 | Kieffer |
| 2010/0292533 A1 | 11/2010 | Kasahara et al. |
| 2011/0022032 A1 | 1/2011 | Zemlok et al. |
| 2011/0275894 A1* | 11/2011 | Mackin ............... A61B 1/00016 600/109 |
| 2012/0059226 A1 | 3/2012 | Funt |
| 2012/0078060 A1 | 3/2012 | Swift |
| 2012/0116170 A1 | 5/2012 | Vayser et al. |
| 2013/0018230 A1 | 1/2013 | Su et al. |
| 2013/0021798 A1 | 1/2013 | Chen et al. |
| 2013/0041229 A2 | 2/2013 | Hahn et al. |
| 2013/0102850 A1 | 4/2013 | Fiorella |
| 2013/0102887 A1 | 4/2013 | Thompson et al. |
| 2013/0158345 A1 | 6/2013 | Majlessi |
| 2013/0197313 A1 | 8/2013 | Wan |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |
| 2014/0088371 A1* | 3/2014 | Vayser ............... A61B 1/00135 600/249 |
| 2014/0202459 A1 | 7/2014 | Iqbal |
| 2014/0275790 A1 | 9/2014 | Vivenzio et al. |
| 2014/0309499 A1 | 10/2014 | Swift |
| 2014/0316211 A1 | 10/2014 | Hermle |
| 2014/0323800 A1 | 10/2014 | Dye |
| 2014/0364695 A1 | 12/2014 | Nadershahi et al. |
| 2014/0371536 A1 | 12/2014 | Miller et al. |
| 2015/0018625 A1 | 1/2015 | Miraki et al. |
| 2015/0157469 A1 | 6/2015 | Prado et al. |
| 2015/0238070 A1 | 8/2015 | Lia et al. |
| 2015/0285382 A1 | 10/2015 | Kienreich et al. |
| 2016/0030128 A1 | 2/2016 | Duggal et al. |
| 2016/0066915 A1 | 3/2016 | Baber et al. |
| 2016/0081833 A1 | 3/2016 | Leblanc et al. |
| 2016/0100751 A1 | 4/2016 | Davis et al. |
| 2016/0151058 A1 | 6/2016 | Ferro et al. |
| 2016/0302657 A1 | 10/2016 | Hussey et al. |
| 2017/0007228 A1 | 1/2017 | Costabile |
| 2017/0020621 A1 | 1/2017 | Huldin et al. |
| 2017/0065282 A1 | 3/2017 | Mathis et al. |
| 2017/0172404 A1 | 6/2017 | McMahon et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 8/2017 | Vayser |
| 2017/0231712 A1* | 8/2017 | Vayser ............... A61B 1/0638 348/68 |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0214013 A1* | 8/2018 | Casson ................ A61B 1/015 |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0271581 A1 | 9/2018 | Yang et al. |
| 2018/0280011 A1 | 10/2018 | Ferro et al. |
| 2018/0296082 A1 | 10/2018 | Salvati et al. |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2018/0336474 A1 | 11/2018 | Vayser et al. |
| 2018/0344144 A1 | 12/2018 | Bouquet |
| 2018/0353059 A1 | 12/2018 | Tesar |
| 2018/0360301 A1 | 12/2018 | Kucklick |
| 2019/0038273 A1 | 2/2019 | Perler et al. |
| 2019/0049655 A1 | 2/2019 | Zagatsky et al. |
| 2019/0076138 A1 | 3/2019 | Opperman |
| 2019/0083079 A1 | 3/2019 | Shimizu et al. |
| 2019/0133432 A1 | 5/2019 | Tsai |
| 2019/0143006 A1 | 5/2019 | Vayser et al. |
| 2019/0143414 A1 | 5/2019 | Vayser et al. |
| 2019/0150422 A1 | 5/2019 | Welch |
| 2019/0150725 A1 | 5/2019 | Ramanujam et al. |
| 2019/0150739 A1 | 5/2019 | Wawro et al. |
| 2019/0150786 A1 | 5/2019 | Vassallo et al. |
| 2019/0167111 A1 | 6/2019 | Greenstein et al. |
| 2019/0167378 A1 | 6/2019 | Wood et al. |
| 2019/0190293 A1 | 6/2019 | Wawro et al. |
| 2019/0223708 A1 | 7/2019 | Recanati et al. |
| 2019/0254512 A1 | 8/2019 | Spiertz |
| 2019/0254771 A1* | 8/2019 | Swift .................. A61B 90/30 |
| 2019/0335988 A1 | 11/2019 | Lia et al. |
| 2019/0343379 A1 | 11/2019 | Altamura |
| 2019/0365217 A1 | 12/2019 | Hegenberger |
| 2020/0008694 A1 | 1/2020 | Karla et al. |
| 2020/0046216 A1 | 2/2020 | Moein |
| 2020/0069171 A1 | 3/2020 | Miller et al. |
| 2020/0107714 A1 | 4/2020 | Bar-Or et al. |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 102415869 A | 4/2012 |
| CN | 302536685 S | 8/2013 |
| CN | 203591245 U | 5/2014 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| DE | 202010017638 U | 5/2012 |
| EP | 0190014 A2 | 8/1986 |
| FR | 2490478 A1 | 3/1982 |
| GB | 2505463 A | 5/2014 |
| RU | 2187972 C2 | 8/2002 |
| RU | 2308873 C2 | 10/2007 |
| WO | 9825512 A1 | 6/1998 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2009137017 A2 | 11/2009 |
| WO | 2013-044151 A1 | 3/2013 |
| WO | 2014-041172 A1 | 3/2014 |

(56) References Cited

FOREIGN PATENT DOCUMENTS

WO 2006121530 A2 11/2016
WO 2016196788 A1 12/2016

OTHER PUBLICATIONS

International Search Report for International application No. PCT/US2016/016154 dated May 19, 2016 for corresponding U.S. application, U.S. Appl. No. 14/614,413.

International Search Report, for International application No. PCT/US2016/035508 dated Sep. 15, 2016 for corresponding U.S. application, U.S. Appl. No. 15/171,581.

International Search Report for International application No. PCT/US2016/036833 dated Jan. 19, 2017.

U.S. Patent references 121-125 and U.S. Published Patent Application references 48 and 50 were cited in an Office Action issued in U.S. Appl. No. 15/171,581.

U.S. Published Patent Application references 47, 49 and 51 were cited in a PCT Search Report issued in PCT Application No. PCT/US2017/042617.

Solvey, Techinical Data Sheet, Ixef 1022 polyarylamide, Feb. 13, 2015, pp. 1-5.

http://www.makeitfrom.com/material-properties/Polyetheretheketone-PEEK, printed on Oct. 9, 2016, pp. 1-9.

The above foreign patent documents were cited in a Nov. 1, 2017 Chinese Office Action, which is enclosed without an English Translation, that issued in Chinese Patent Application No. 2017102800054450.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

The above patent was cited in a Oct. 29, 2018 Chinese Office Action, which is enclosed without an English Translation, that issued in Chinese Patent Application No. 201711159829.6.

The above documents were cited in a European Search Report dated Nov. 23, 2018, which is enclosed, that issued in the corresponding European Patent Application No. 16747107.7.

The above U.S. Publications documents #1 and #2 were cited in a Supplementary European Search Report dated Apr. 24, 2019, which is enclosed, that issued in European Patent Application No. 16804432.9.

Redefining illumination, Eikon LT Adapt SE For optimal precision and protection (2019), Stryker, www.stryker.com/surgical (3 pages).

\* cited by examiner ered. The particularly an surgical instru-
ILLUMINATED SUCTION DEVICE

CROSS-REFERENCE TO RELATED APPLICATIONS

This application claims priority to U.S. Provisional Pat. App. No. 62/441,645, filed on Jan. 3, 2017, and entitled "Illuminated Suction Device", and claims priority to U.S. Provisional Pat. App. No. 62/360,810, filed on Jul. 11, 2016, and also entitled "Illuminated Suction Device". The entire contents of each of those applications are incorporated herein by reference.

INTRODUCTION

Embodiments described herein relate to a surgical instrument and more particularly to an instrument which is especially well suited for the removal of body fluids such as blood from a surgical wound and for simultaneously illuminating an area of the wound so that the same can be visualized by a surgeon.

It is often necessary during the course of a surgical procedure for body fluids, such as blood, to be removed from the area of the surgical wound in order that the same may be visualized by the surgeon. The arrangements hitherto provided for the removal of such fluids from and for the illumination of surgical wounds have left much to be desired.

This may be better appreciated when it is understood that it is often necessary to maintain a surgical suction device in place in the wound in order to permit the surgeon to visualize the point at which the bleeding has occurred. Particularly when such a suction device is in place, it is extremely difficult and often impossible to prevent the suction device from interfering with the desired visualization and illumination.

Hand-held suction devices are routinely used during surgical procedures. These devices are typically connected to a standard suction source in the operating room, enabling the physician to dynamically and efficiently remove blood, bone fragments, or fluid previously irrigated into the surgical site. These suction devices are sometimes also used to provide low force retraction of fat, muscle, or other structures during the procedure. The surgeon holds the suction device from its proximal end, manipulating the distal portion of the suction device during the surgical procedure in order to provide suction at the desired location. Hand-held suction devices are widely available in a variety of distal tip configurations suited to various surgical applications.

A Yankauer suction device is a medical instrument that provides suction to a wound or other surgical incision to remove fluids from the area. Yankauer suction devices come in a metal version (as shown in FIG. 1) and a plastic version (as shown in FIG. 2). The plastic version depicted in FIG. 2 is a sterile, single-use suction tool used to remove mucus from the mouth, primarily from the throat. The Yankauer suction device in FIG. 2 is rigid and has a curved one-piece design made with shatterproof acrylics plastic.

One end of the depicted Yankauer suction device is connected to a tubing (which provides the suction) that can work with suction machine devices, and the other end is inserted into the area to be evacuated. The devices may come with several style tips. Some have a hole at the end and some have additional holes on the sides.

FIG. 2 shows a device having a hole in the top of the handle. This hole may be used by the operator to control the suction at the tip. If the operator covers the hole with his thumb the full suction will be present at the tip. Opening the hole will dramatically reduce the suction at the tip.

Alternatively, referring to FIG. 3, a Yankauer suction device may have a built-in shutoff valve, which may be used by the operator to control the suction at the tip.

However, none of the traditional suction devices have a permanent, integral light source. Most lack any light source, requiring the operator to provide an external light source. This external light source is often difficult to direct into deep tissue cavities, leaving the operator with limited visibility into the patient cavity.

FIG. 4 shows a recent improvement of a built-in light channel that provides light to the tip of the suction device. Unfortunately, this light channel is not a light source. The light source in this product is a portable external laser unit, connected to the suction device via a fiber optic cable. Such suction devices with optic cables present additional cabling problems during the procedure, cleaning problems between procedures, and cost problems (the laser sources are expensive, as are the fiber optic cables).

One or more embodiments described herein advantageously provide a suction and illumination device which is especially well suited for use in carrying out surgical procedures and which provides for simultaneous evacuation of fluids from and illumination of a surgical wound.

One or more embodiments described herein advantageously provide a hand-held illuminated suction device that includes suction and illumination functions irremovably integrated into the device.

One or more embodiments described herein advantageously provide a disposable suction device to enable leverage of manufacturing efficiencies.

One or more embodiments described herein advantageously provide a low cost, high-performance combination device that provides an attractive alternative to existing discrete illumination and suction devices while minimizing incremental cost to the user.

LEGEND

Figure 1:
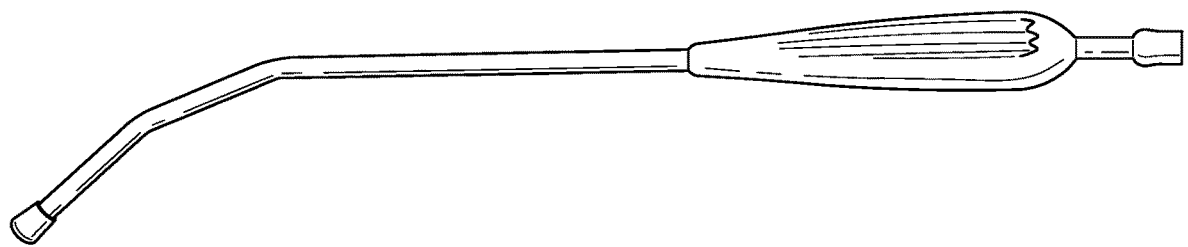
FIG. 1 is a schematic view of a conventional suction device made of metal.
Figure 2:
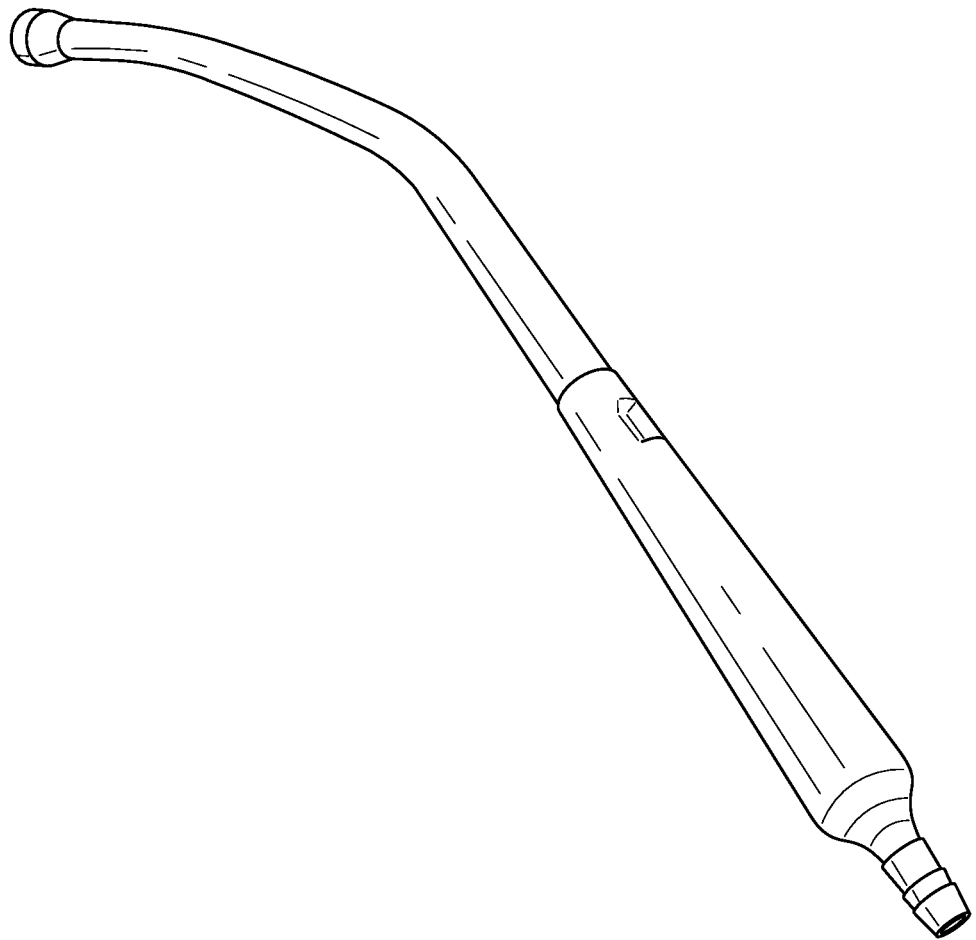
FIG. 2 is a schematic view of a conventional suction device made of plastic.
Figure 3:
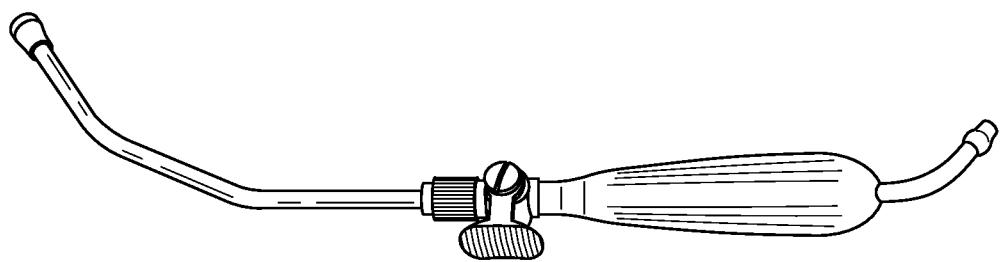
FIG. 3 is a schematic view of a conventional suction device having a built-in shutoff valve.
Figure 4:
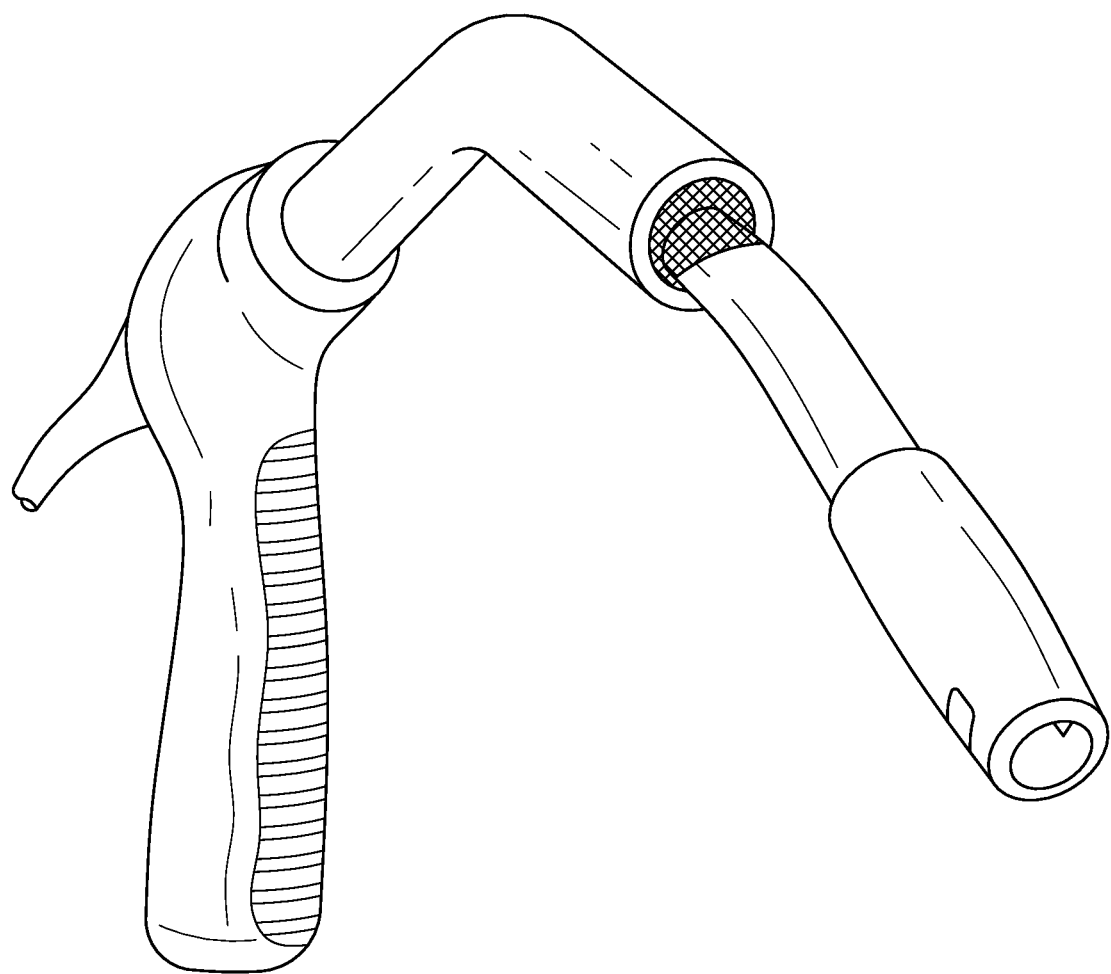
FIG. 4 is a schematic view of a conventional suction device having a light channel connected to an external laser unit.

In the drawings, the following legend applies to the use of reference numerals.
- 10 suction device
- 11 LED
- 12 LED wires
- 13 illumination switch
- 14 battery pack
- 15 suction device
- 16 suction control switch
- 17 grip

DETAILED DESCRIPTION OF SELECT EXEMPLARY EMBODIMENTS

Drawings have been used herein to depict select exemplary embodiments. For the sake of clear illustration, many practical details are explained together in the description below. However, it should be appreciated that those details should not be used to limit the scope of any claims that issue in connection with this application. In some embodiments, certain details are not essential.

Moreover, for the sake of drawing simplification, some customary structures and elements in the drawings have been shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art. It should be further understood that terms, such as those defined in commonly used dictionaries, should be interpreted as having a meaning that is consistent with their meaning in the context of the relevant art and the present description, and should not be interpreted in an idealized or overly formal sense unless expressly so defined herein.

Figure 5:
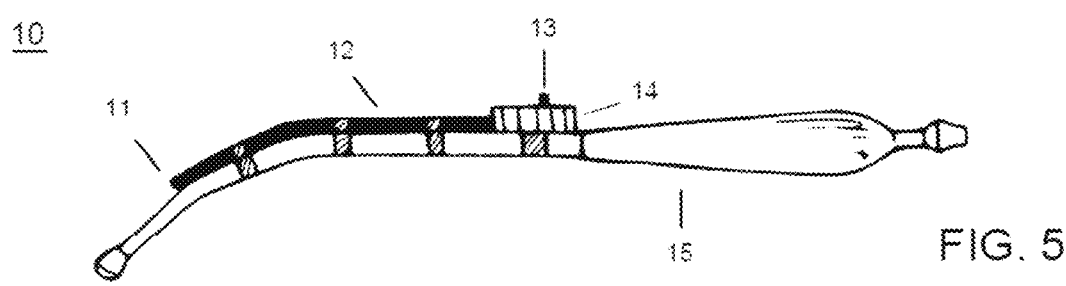
FIG. 5 is a schematic view of an illuminated suction device according to a first exemplary embodiment.

FIG. 5 is a schematic view of an illuminated suction device according to an exemplary embodiment. An illuminated suction device 15 includes suction and illumination functions integrated into a hand-held device. As shown in FIG. 5, the illuminated suction device 15 has a proximal end and a distal end connected by a central portion. The proximal end of the suction tube is provided with fittings for connection to a vacuum source, while the distal end enables the operator to apply the suction device directly to the desired region. The illuminated suction device 15 may be constructed with a permanent light source, such as LED 11. LED 11 is powered by battery pack 14 and is directly and permanently embedded into the central portion of the suction device 15. The battery pack 14 is connected to LED 11 through LED wires 12 and provides power to LED 11.

The battery or batteries in battery pack 14 may be sized to contain only enough charge to illuminate a single procedure, thus offering energy-efficient, low-cost illumination. With the low cost LED illumination, the suction device (integrating suction and illumination functions) may be (mandatorily) disposable after a single use. This solves the illumination problem, and also solves the problems of cost, cabling, and cleaning/sterilization.

Alternatively, the batteries may be sized to contain sufficient charge to illuminate multiple procedures. The illuminated suction device may also include an illumination switch 13 for switching LED 11 between ON/OFF status.

In this embodiment, illumination switch 13 may located above the battery pack 14. Illumination switch 13 may be a light dimmer switch, which allows an operator to control the level of illumination. Switch 13 may alternatively be a pull-tab switch, further mandating that the device be disposed of after a single use, or may be any other type of suitable switch, as will be apparent to those skilled in the art.

Figure 6:
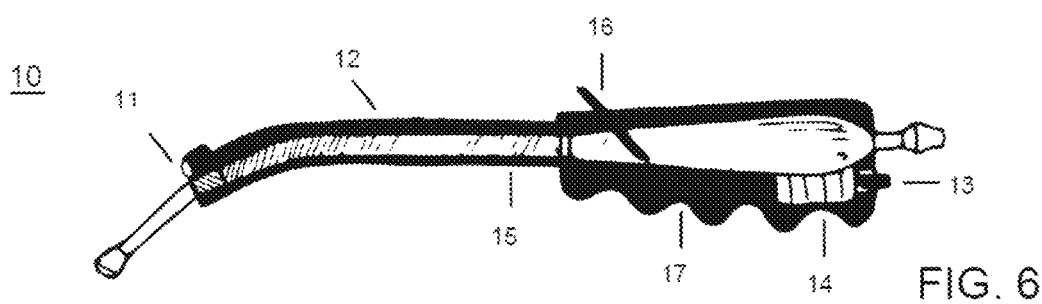
FIG. 6 is a schematic view of an illuminated suction device according to a second exemplary embodiment.
Figure 7:
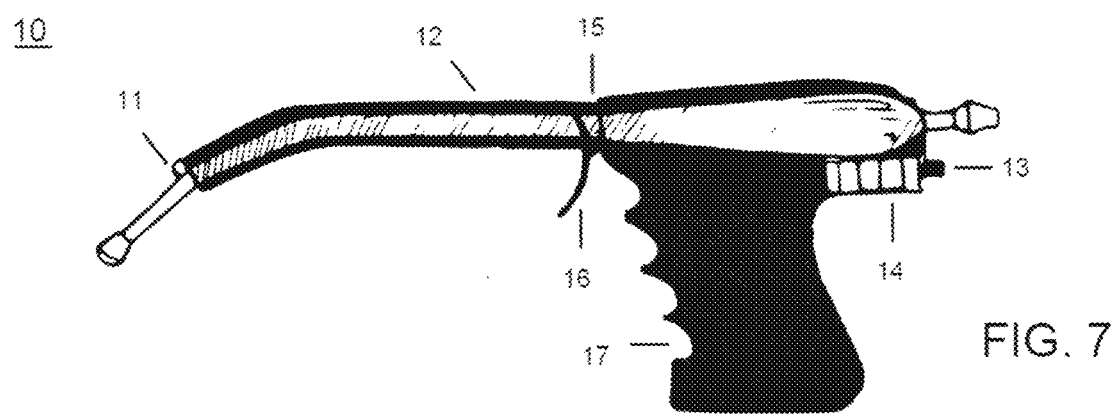
FIG. 7 is a schematic view of an illuminated suction device according to a third exemplary embodiment.
Figure 8:
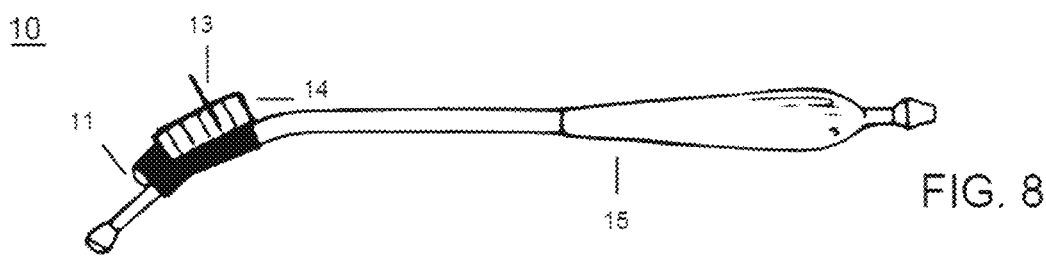
FIG. 8 is a schematic view of an illuminated suction device according to a fourth exemplary embodiment.

In other embodiments, switch 13 may be located at the proximal end of the device (see FIGS. 6 and 7), or at the distal end (see FIG. 8).

In other embodiments, switch 13 may be replaced with a magnetic reed switch located in close proximity to the suction shut off valve and a magnet is embedded into the shut off valve such that the act of opening the shutoff valve will also move the magnet into close proximity to the reed switch and thus active the reed switch and turn on the light. This embodiment enables one control to be used for both the shutoff valve as well as the light switch. Those skilled in the art will understand how sliding the shutoff valve open or partially open can move an imbedded magnet towards a fixed position reed switch which is embedded in the body of the suction device in such a location to activate the magnetic reed switch when the suction valve is open or partially open and deactivate the magnetic reed switch when the shutoff valve is closed. Those skilled in the art will see that the magnetic reed switch can be replaced with other proximity sensors such as hall effect sensors to replicate the convenience created by having one control activate both the suction and the light source.

In other embodiments the LED (11) may directly shine light toward the distal end of the suction device, or may direct light into the clear plastic shaft of the suction device where the light may be conducted and then dispersed from integral lenses at or near the distal tip of the suction device.

With respect to materials, one exemplary aspect comprises an illuminated suction device, comprising: a distal end having a suction tip; a proximal end having a connector for a suction tube; and an illumination assembly comprising at least one light source, at least one battery and an activation device for energizing the light source, and the illumination assembly being permanently attached to the suction device, wherein the suction device is molded from at least one of: an injection moldable polymer, a low conductivity polymer, and a radiolucent polymer. In one or more embodiments the polymer may have a conductivity of less than $10^{-6}$ A.

Figure 9:
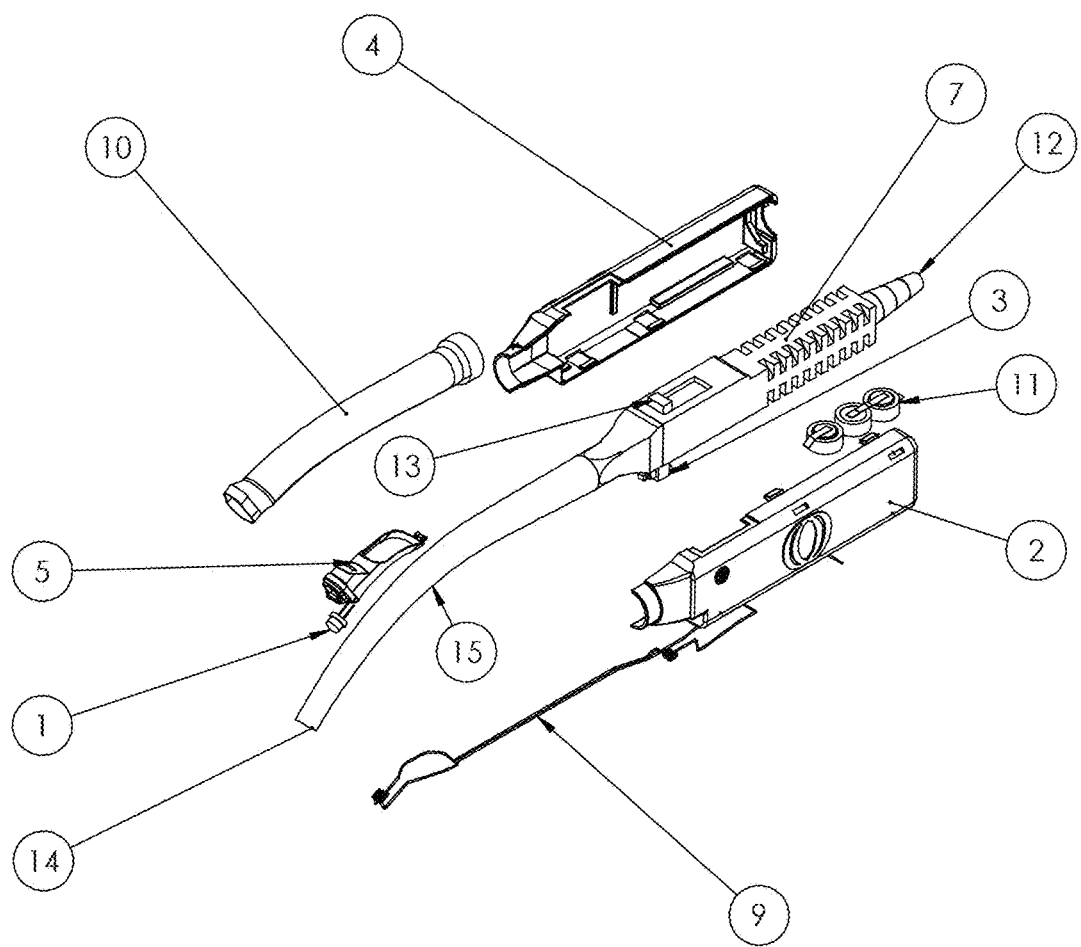
FIG. 9 depicts a disassembled version of an exemplary embodiment.

FIG. 9 depicts a disassembled version of an exemplary embodiment.

Item 7 is the handle portion of a standard Yankauer suction device.

Item 12 is the connection port for attaching a suction hose.

Item 14 is the distal end of the Yankauer suction device which is used to remove fluid from the patient. Item 14 can be of different shapes to facilitate the type of suction needed. Existing art includes a straight end as shown (14), or a ball end which facilitates suction from the sides of the ball (not shown).

Item 13 is a suction valve which inhibits or restricts the connection between the suction port (12) and the suction input (14).

Item 11 is the battery pack which contains sufficient charge for a single use. It may be (and preferably is) disposable and thus compatible with medical waste procedures which include safe incineration. Battery chemistry such as alkaline batteries are compatible with incineration.

Item 9 are connecting wires that make the circuit between the switch (3), the batteries (11) and the LED (1).

Item 5 is an LED holder that is shaped such that it can easily fit over a ball end (at location 14) but still fit flush against the length portion of the suction tube (15).

Items 4 and 2 are covers which contain the Yankauer suction device (7), the batteries (11), the switch (3), and a portion of the wire (9).

Item 10 is a shrink wrap which fits over a portion of the LED holder (5), a portion of the suction tube length (15), a portion of the wire (9), and a portion of the covers (4) and (2). This shrink wrap preferably has several unique properties to the assembly. The shrink wrap shrinks in diameter when heat is applied. After it is properly placed and heated it will shrink to anchor the LED holder (5), wire (9) and the ends of covers (4) and (2). No additional and expensive anchoring is required.

Although all components are properly anchored in position, the shrink wrap still allows the normal flexibility of the Yankauer length portion (14). This flexibility is important to operation during a medical procedure as the Yankauer is often pressed against patient tissue and the Yankauer flexing helps prevent tissue damage and increases patient safety. Although shrink wrap is used in this embodiment, those skilled in the art will understand that other means of attachment, such as welding, adhesives, etc., may also be used without departing from the scope of the invention described herein.

In an embodiment, a light source comprises at least one lamp and at least one battery within a container permanently affixed to the suction device, wherein a longitudinal side of the container opens onto a side of the suction device such that the container and the side together circumferentially enclose and secure the at least one battery to the device.

In an embodiment, the illumination assembly (i.e., at least the light source and at least one battery) is enclosed within a container permanently affixed to the suction device, wherein a longitudinal side of the container opens onto a side of the suction device such that the container and the side together circumferentially enclose and secure the at least one battery to the device.

Figure 10:
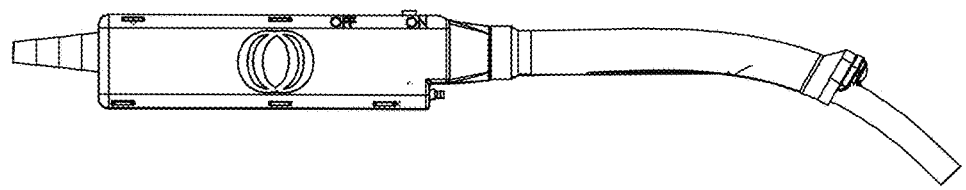
FIGS. 10-12 depict an embodiment of the assembled device.
Figure 11:
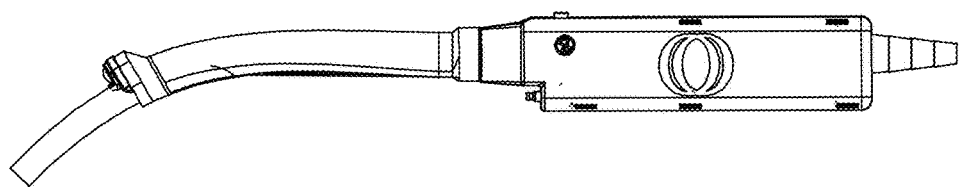
Figure 12:

FIGS. 10-12 depict the assembled device.

Although certain embodiments have been described in considerable detail herein, other embodiments, variations, and modifications that fall within the spirit and scope of the invention will be apparent to those skilled in the art. Therefore, the scope of any claims allowed for this application should not be limited to any specific embodiments or to any non-claimed details of the embodiments described herein.

I claim:

1. An illuminated suction device comprising:
   a suction tube having a distal end with a suction tip and a proximal end with a connector;
   a handle adjacent the proximal end of the suction tube; and
   an illumination assembly comprising at least one light source, at least one battery, and an activation device for energizing the light source, the illumination assembly being attached to the suction device,
   wherein the at least one light source is provided at a location closer o the distal end than to the proximal end of the suction tube and is axially offset from the distal end along the axis of the suction tube, and
   wherein the illumination assembly is enclosed within a container, wherein a longitudinal side of the container opens onto a side of the suction tube such that the container and the side together circumferentially enclose and secure the illumination assembly to the suction tube.

2. An illuminated suction device as in claim 1, wherein the suction device is molded from at least one of: an injection moldable polymer, a low conductivity polymer, and a radiolucent polymer.

3. An illuminated suction device as in claim 1, configured to provide simultaneous evacuation of fluids from and illumination of a surgical wound.

4. An illuminated suction device as in claim 1, wherein the container includes shrink-wrap attached to the suction tube.

5. An illuminated suction device as in claim 1, wherein the light source is an LED light.

6. An illuminated suction device as in claim 1, wherein the light source is embedded into the suction tube.

7. An illuminated suction device as in claim 1, wherein the activation device comprises at least one of: a pull-tab switch and a dimmer switch.

8. An illuminated suction device as in claim 1, wherein the light source shines directly toward the distal end of the suction tube.

9. An illuminated suction device as in claim 1, wherein the light source directs light into a shaft of the suction tube, and light from the light source is dispersed from one or more lenses in the distal end.

10. An illuminated suction device as in claim 1, wherein the distal end comprises a ball.

11. An illuminated suction device as in claim 1, wherein opening of a suction valve of said device causes the activation device to be activated.

12. An illuminated suction device as in claim 11, further comprising a magnet embedded into the suction valve, and wherein:
    the activation device comprises a magnetic reed switch, and
    the magnet embedded into the suction valve is moved closer to the activation device when the suction valve is opened.

13. An illuminated suction device as in claim 11, further comprising a magnet embedded into the suction valve, and wherein:
    the activation device comprises a Hall effect sensor, and
    the magnet embedded into the suction valve is moved closer to the activation device when the suction valve is opened.

14. The illuminated suction device in accordance with claim 1, wherein the at least one light source is provided at a location external to the handle.

15. The illuminated suction device in accordance with claim 1, wherein the suction tube includes a curved portion and wherein the at least one light source is provided adjacent the curved portion.

16. An illuminated suction device comprising:
    a distal end with a suction tip;
    a proximal end with a connector for a suction tube;
    a suction valve configured to control suction by the suction device; and
    an illumination assembly comprising at least one light source, at least one battery, and an activation device for energizing the light source, the illumination assembly being attached to the suction device,
    wherein opening of the suction valve of said device causes the activation device to be activated.

17. The illuminated suction device in accordance with claim 16, further comprising a magnet embedded into the suction valve, and wherein:
    the activation device comprises one of a magnetic reed switch and a Hall effect sensor, and the magnet embedded into the suction valve is moved closer to the activation device when the suction valve is opened.

\* \* \* \* \*